United States Patent
Bui et al.

(10) Patent No.: US 9,308,396 B2
(45) Date of Patent: *Apr. 12, 2016

(54) TRANSFER-RESISTANT AND LONG WEAR FOUNDATION IN EMULSION FORM CONTAINING OIL ABSORBING POWDERS

(75) Inventors: Hy Si Bui, Piscataway, NJ (US); Mohamed Kanji, Edison, NJ (US); Susan Halpern, Paramus, NJ (US)

(73) Assignee: L'OREAL, Paris (FR)

( * ) Notice: Subject to any disclaimer, the term of this patent is extended or adjusted under 35 U.S.C. 154(b) by 22 days.

This patent is subject to a terminal disclaimer.

(21) Appl. No.: 13/140,083

(22) PCT Filed: Dec. 16, 2009

(86) PCT No.: PCT/US2009/068139
§ 371 (c)(1),
(2), (4) Date: Aug. 17, 2011

(87) PCT Pub. No.: WO2010/077887
PCT Pub. Date: Jul. 8, 2010

(65) Prior Publication Data
US 2011/0300087 A1  Dec. 8, 2011

Related U.S. Application Data

(60) Provisional application No. 61/122,831, filed on Dec. 16, 2008, provisional application No. 61/122,834, filed on Dec. 16, 2008.

(51) Int. Cl.
*A61K 8/84* (2006.01)
*A61K 8/92* (2006.01)
*A61Q 1/02* (2006.01)
*A61K 8/25* (2006.01)
*A61K 8/81* (2006.01)

(52) U.S. Cl.
CPC ... *A61Q 1/02* (2013.01); *A61K 8/25* (2013.01); *A61K 8/8164* (2013.01); *A61K 8/84* (2013.01); *A61K 8/92* (2013.01)

(58) Field of Classification Search
CPC .......... A61K 8/25; A61K 8/8164; A61K 8/84; A61K 8/92; A61Q 1/02
USPC .......................................................... 424/63
See application file for complete search history.

(56) References Cited

U.S. PATENT DOCUMENTS

| | | | |
|---|---|---|---|
| 2,957,838 A | 10/1960 | Mills, Jr. | |
| 3,590,076 A | 6/1971 | Heintzelman et al. | |
| 3,699,154 A | 10/1972 | Heintzelman et al. | |
| 3,933,511 A | 1/1976 | Heintzelman et al. | |
| 3,933,512 A | 1/1976 | Heintzelman et al. | |
| 4,041,056 A | 8/1977 | Heintzelman et al. | |
| 4,226,889 A | 10/1980 | Yuhas | |
| 4,420,588 A | 12/1983 | Yoshioka et al. | |
| 4,444,749 A * | 4/1984 | Rouet ........................ | 424/70.17 |
| 4,871,536 A | 10/1989 | Arraudeau et al. | |
| 5,032,391 A | 7/1991 | Helioff et al. | |
| 5,389,363 A | 2/1995 | Snyder et al. | |
| 5,618,524 A | 4/1997 | Bolich et al. | |
| 5,620,693 A | 4/1997 | Piot et al. | |
| 5,800,816 A | 9/1998 | Brieva et al. | |
| 5,911,974 A | 6/1999 | Brieva et al. | |
| 5,965,112 A | 10/1999 | Brieva et al. | |
| 5,985,298 A | 11/1999 | Brieva et al. | |
| 5,998,547 A | 12/1999 | Hohner | |
| 6,126,929 A | 10/2000 | Mougin | |
| 6,274,152 B1 | 8/2001 | Brieva et al. | |
| 6,464,964 B1 | 10/2002 | Brieva et al. | |
| 6,482,400 B1 | 11/2002 | Collin | |
| 6,492,455 B1 | 12/2002 | Nadolsky | |
| 6,503,495 B1 * | 1/2003 | Alwattari et al. ............ | 424/70.7 |
| 6,524,564 B1 | 2/2003 | Kim et al. | |
| 6,562,322 B2 | 5/2003 | Brieva et al. | |
| 6,716,419 B2 | 4/2004 | Zoltowski et al. | |
| 6,780,422 B2 | 8/2004 | Brieva et al. | |
| 6,958,148 B1 | 10/2005 | Green et al. | |
| 7,005,134 B2 | 2/2006 | Brieva et al. | |
| 7,160,550 B2 | 1/2007 | Brieva et al. | |
| 7,186,766 B2 | 3/2007 | Harashina et al. | |
| 7,314,904 B2 | 1/2008 | Nadolsky et al. | |

(Continued)

FOREIGN PATENT DOCUMENTS

DE       100 64 799 A1   6/2002
DE    102004008941 A1   9/2005

(Continued)

OTHER PUBLICATIONS

Cosmetic Business 2008 Conference Program (published: May 6, 2008).*
U.S. Appl. No. 13/133,179, filed Aug. 2, 2011, Bui, et al.
U.S. Appl. No. 13/133,187, filed Aug. 31, 2011, Bui, et al.
U.S. Appl. No. 13/132,724, filed Aug. 11, 2011, Bui, et al.
U.S. Appl. No. 13/132,811, filed Jul. 29, 2011, Bui, et al.
International Search Report issued Jul. 28, 2010 in PCT/US09/68139 filed Dec. 16, 2009.
European Office Action Issued Feb. 22, 2013 in Patent Application No. 10 167 788.8.
Hauthal, H. G. Basics, Ingredients, Detergents, Product Safety and Sustainability. Tenside Surf. Det. Jan. 2008, 45 (1), 30-42.
Vertellus, ZeMac(R) E400 Copolymer Technical Data Sheet, May 29, 2008.
European Search Report dated Mar. 10, 2011, in European Application No. 10167784.7.
European Office Action from European Patent Application No. 10167784.7 dated Mar. 21, 2011 (4 pages).
L. Rudnick, Synthesis, Mineral Oils, and Bio-Based Lubricants, Chemistry and Technology.

(Continued)

*Primary Examiner* — Anoop Singh
*Assistant Examiner* — Doan Phan
(74) *Attorney, Agent, or Firm* — Oblon, McClelland, Maier & Neustadt, L.L.P.

(57) ABSTRACT

The present invention is directed to a transfer resistant and long wear cosmetic composition having a unique gel-like texture with good pickup, payoff, and spreadability properties, as well as a silky smooth feel containing: (a) at least one polyamine; (b) at least one oil-soluble polar modified polymer; (c) water; (d) at least one volatile solvent; (e) at least one non-volatile solvent; (f) at least one water soluble surfactant; (f) at least one colorant; and (g) at least one oil absorbing powder.

6 Claims, No Drawings

(56) References Cited

U.S. PATENT DOCUMENTS

| | | |
|---|---|---|
| 7,423,104 B2 | 9/2008 | Lion |
| 7,682,621 B2 | 3/2010 | Lamberty et al. |
| 7,875,265 B2 | 1/2011 | Blin et al. |
| 8,119,110 B2 | 2/2012 | Blin et al. |
| 2003/0026816 A1 | 2/2003 | Zoltowski et al. |
| 2003/0082126 A9* | 5/2003 | Pinzon et al. ............... 424/70.11 |
| 2003/0082218 A1 | 5/2003 | Ichinohe et al. |
| 2003/0147931 A1 | 8/2003 | Brieva et al. |
| 2003/0182734 A1 | 10/2003 | Desenne et al. |
| 2004/0170586 A1 | 9/2004 | Ferrari et al. |
| 2004/0186308 A1 | 9/2004 | Koch et al. |
| 2004/0223986 A9* | 11/2004 | Boussouira et al. ........... 424/401 |
| 2005/0013992 A1 | 1/2005 | Azad et al. |
| 2005/0180936 A1 | 8/2005 | Pays |
| 2005/0220728 A1 | 10/2005 | Kanji et al. |
| 2006/0013840 A1 | 1/2006 | Lamberty et al. |
| 2006/0039886 A1* | 2/2006 | Shefer et al. ..................... 424/73 |
| 2006/0084764 A1 | 4/2006 | Hanna et al. |
| 2006/0093568 A1 | 5/2006 | Blin et al. |
| 2006/0104940 A1 | 5/2006 | Heinrichs et al. |
| 2006/0110345 A1 | 5/2006 | Lu et al. |
| 2006/0110415 A1* | 5/2006 | Gupta ............................ 424/401 |
| 2006/0115444 A1 | 6/2006 | Blin et al. |
| 2006/0128592 A1* | 6/2006 | Ross et al. ..................... 510/439 |
| 2006/0147396 A1 | 7/2006 | Monello |
| 2006/0147402 A1 | 7/2006 | Blin et al. |
| 2006/0159642 A1 | 7/2006 | Hanna et al. |
| 2006/0165626 A1 | 7/2006 | Ricard et al. |
| 2006/0188459 A1 | 8/2006 | Heinrichs et al. |
| 2006/0228312 A1 | 10/2006 | Weiss et al. |
| 2006/0286057 A1 | 12/2006 | Cannell et al. |
| 2007/0031361 A1 | 2/2007 | Herrmann et al. |
| 2007/0092468 A1 | 4/2007 | Brieva et al. |
| 2007/0110700 A1 | 5/2007 | Wells et al. |
| 2007/0110702 A1 | 5/2007 | Ehara |
| 2007/0134181 A1 | 6/2007 | Shimizu et al. |
| 2007/0212315 A1 | 9/2007 | Pastor et al. |
| 2007/0256700 A1 | 11/2007 | Bodelin |
| 2007/0258932 A1 | 11/2007 | Bui et al. |
| 2007/0259012 A1 | 11/2007 | Castro et al. |
| 2008/0025934 A1 | 1/2008 | Lebre et al. |
| 2008/0044445 A1* | 2/2008 | Rubin ............................ 424/401 |
| 2008/0199420 A1* | 8/2008 | Wendel et al. ............. 424/78.02 |
| 2008/0207871 A1 | 8/2008 | Seiler et al. |
| 2009/0060959 A1 | 3/2009 | Igarashi |
| 2009/0130037 A1 | 5/2009 | Thevenet et al. |
| 2010/0310489 A1 | 12/2010 | Barba |
| 2010/0330012 A1 | 12/2010 | Bui et al. |
| 2010/0330015 A1 | 12/2010 | Bui et al. |
| 2010/0330016 A1 | 12/2010 | Bui et al. |
| 2010/0330017 A1 | 12/2010 | Bui et al. |
| 2010/0330022 A1 | 12/2010 | Bui et al. |
| 2010/0330024 A1 | 12/2010 | Bui et al. |
| 2011/0020254 A1 | 1/2011 | Bui et al. |
| 2011/0020255 A1 | 1/2011 | Bui et al. |
| 2011/0020256 A1 | 1/2011 | Bui et al. |
| 2011/0020257 A1 | 1/2011 | Bui et al. |
| 2011/0020260 A1 | 1/2011 | Bui et al. |
| 2011/0020261 A1 | 1/2011 | Bui et al. |
| 2011/0020263 A1 | 1/2011 | Ilekti et al. |
| 2011/0021681 A1 | 1/2011 | Bui et al. |
| 2011/0021683 A1 | 1/2011 | Bui et al. |
| 2011/0038819 A1 | 2/2011 | Bui et al. |
| 2011/0223122 A1 | 9/2011 | Bui et al. |
| 2011/0223123 A1 | 9/2011 | Bui et al. |
| 2011/0280817 A1 | 11/2011 | Ramadan et al. |
| 2011/0280818 A1 | 11/2011 | Kawaratani et al. |
| 2011/0280820 A1 | 11/2011 | Bui et al. |
| 2011/0286950 A1 | 11/2011 | Bui et al. |
| 2011/0286951 A1 | 11/2011 | Bui et al. |
| 2011/0293550 A1 | 12/2011 | Bui et al. |
| 2011/0311467 A1 | 12/2011 | Bui et al. |
| 2012/0004327 A1 | 1/2012 | Bui et al. |
| 2012/0107263 A1 | 5/2012 | Bui et al. |
| 2012/0171137 A1 | 7/2012 | Bradsaw et al. |
| 2012/0171139 A1 | 7/2012 | Bradshaw et al. |

FOREIGN PATENT DOCUMENTS

| | | | |
|---|---|---|---|
| EP | 1 314 415 A1 | | 5/2003 |
| EP | 1 854 451 A2 | | 11/2007 |
| EP | 1680070 B1 | * | 4/2008 |
| EP | 2 036 536 A1 | | 3/2009 |
| JP | A-07053921 | | 2/1995 |
| WO | WO 96/03967 A1 | | 2/1996 |
| WO | WO 01/17485 | | 3/2001 |
| WO | WO 02/088456 A1 | | 11/2002 |
| WO | WO 02 098379 A1 | | 12/2002 |
| WO | WO 2006/112690 A1 | | 10/2006 |
| WO | WO 2006/127883 A2 | | 11/2006 |
| WO | WO 2007014939 A1 | * | 2/2007 |
| WO | WO 2007/048672 A1 | | 5/2007 |
| WO | WO 2007/096400 A1 | | 8/2007 |
| WO | WO 2007/139812 A2 | | 12/2007 |
| WO | WO 2008/046763 A1 | | 4/2008 |
| WO | WO 2009/085888 A1 | | 7/2009 |

OTHER PUBLICATIONS

Perstorp, Boltorn® II20 product data sheet dated Jan. 3, 2008.
Perstorp, Determination of Viscosity for Boltorn Dendritic Polymers, Aug. 23, 2011.
Mulkern et al. Polymer, 2000, 41 (9), 3193-3203.
Bergbreiter et al. Tetrahedron Letters, 1997, 38 (21), 3703-3706.
European Search Report issued Apr. 8. 2011, in European Patent Application No. 10167791.2 (with English Abstract).
European Search Report issued Mar. 21, 2011, in European Application No. 10167792.0.
European Search Report issued Apr. 6, 2011, in European Patent Application No. 10167794.6.
European Search Report dated Mar. 14, 2011, issued in European Application No. 10167785.4.
European Patent Office Communication dated Apr. 18, 2011, issued in European Application No. 10167785.4.
European Search Report issued Mar. 10, 2011, in European Application No. 10167790.4.
European Office Action issued in European Patent Application No. 10167790.4 dated Mar. 21, 2011 (4 pages).
International Search Report issued May 20, 2010 in PCT/US09/067332 filed Dec. 9, 2009.
International Search Report issued Aug. 11, 2010 in PCT/US09/68246 filed Dec. 16, 2009.
International Search Report Issued Jul. 26, 2010 in PCT/US09/068151 filed Dec. 16, 2009.
International Search Report issued Jul. 28, 2010 in PCT/US09/68251 filed Dec. 16, 2009.
International Search Report issued Jul. 30, 2010 in PCT/US09/68148 filed Dec. 16, 2009.
http://www.Chemical Book.com/ChemicalProductProperty_EN_CB3748204.htm, Poly (methyl vinyl ether-alt-maleic anhydride), 2010.
International Search Report Issued Jul. 30, 2010 in PCT/US09/068146 filed Dec. 16, 2009.
International Search Report issued Jul. 23, 2010 in PCT/US09/68245 filed Dec. 16, 2009.
Extended European Search Report Issued Nov. 29, 2012 in Patent Application No. 08867867.7.
International Search Report issued May 31, 2010 in PCT/US09/067338 filed Dec. 9, 2009.
Supplementary European Search Report dated Aug. 7, 2014 as received in the corresponding European Patent Application No. 09836856.6-1464 / 2358341.
Database GNPD [Online] Mintel; Dec. 2002, Anonymous: "Skin Equalizing Powder Makeup", XP002726672, Database accession No. 10123605 *the whole document*.
Database GNPD [Online] Mintel; Dec. 2006, Anonymous: "Creamy Concealer to Go", XP002726671, Database accession No. 694045 *the whole document*.

* cited by examiner

US 9,308,396 B2

TRANSFER-RESISTANT AND LONG WEAR FOUNDATION IN EMULSION FORM CONTAINING OIL ABSORBING POWDERS

FIELD OF THE INVENTION

The present invention relates to a colored cosmetic composition which is transfer-resistant, long wearing, with good payoff and texture. Furthermore, the present invention generally relates to a novel composition having superior silky smooth feel and spreadability.

DISCUSSION OF THE BACKGROUND

Many compositions, especially cosmetic compositions, have been developed for easy and comfortable application onto a targeted substrate. Unfortunately, many of these compositions are in fact difficult to apply and do not possess a smooth feel upon application. Moreover, compositions often times have a tendency to feel tacky, yielding poor application and spreadability characteristics. Similarly, the use of silicone resins and other types of film formers to impart transfer resistance onto a colored cosmetic product suffers from the same disadvantages disclosed above.

In general, a gel-like texture is typically obtained with the use of expensive silicone elastomers which are swelled in a solvent. The present invention does not require the use of silicone elastomers in order to achieve the desired gel-like texture. Moreover, silicone elastomers can also be difficult to formulate with due to their chemical make up, and the gelled compositions they form may be unstable, as is, or sensitive to added ingredients.

Similarly, a rigid texture is typically obtained through the use of waxes and wax-like ingredients. The present invention, however, does not require the use of these types of conventionally-employed ingredients in order formulate compositions having a rigid texture. On the contrary, essentially the same ingredients used to formulate a composition having a gel-like texture can be used to formulate one having a more rigid texture. Significant cost reductions are thus realized due to the relatively inexpensive cost of the ingredients used, as well as the ease in formulating such compositions.

Therefore, it is an object of the present invention to provide a composition capable of possessing a unique texture and feel with surprisingly good transfer resistance, long wear, cosmetic pickup and payoff, silky smooth feel and spreadability properties, without having to use silicone resins, silicone elastomers and/or gelling agents.

SUMMARY OF THE INVENTION

The present invention relates to a transfer resistant, long wear composition having good cosmetic pickup and payoff comprising:
(a) at least one polyamine;
(b) at least one oil-soluble polar modified polymer;
(c) water;
(d) at least one volatile solvent other than water;
(e) at least one non-volatile solvent capable of solubilizing the oil-soluble polar modified polymer;
(f) at least one water soluble surfactant;
(g) at least one colorant; and
(h) at least one oil absorbing powder.

The present invention also relates to a transfer resistant, long wear composition having good cosmetic pickup and payoff comprising:
(a) a reaction product of at least one polyamine and at least one oil-soluble polar modified polymer;
(b) water;
(c) at least one volatile solvent other than water;
(d) at least one non-volatile solvent capable of solubilizing the oil-soluble polar modified polymer;
(e) at least one water soluble surfactant;
(f) at least one colorant; and
(g) at least one oil absorbing powder.

The present invention relates to a transfer resistant, long wear composition having good cosmetic pickup and payoff, made by combining ingredients comprising:
(a) at least one polyamine;
(b) at least one oil-soluble polar modified polymer;
(c) water;
(d) at least one volatile solvent other than water;
(e) at least one non-volatile solvent capable of solubilizing the oil-soluble polar modified polymer;
(f) at least one water soluble surfactant;
(g) at least one colorant; and
(h) at least one oil absorbing powder.

Preferably, the composition does not require or contain silicone resins, silicone elastomers and/or gelling agents.

The present invention also relates to methods of making up a keratinous substrate comprising applying the above-disclosed composition onto the substrate.

It has been surprisingly discovered that the above-disclosed composition possesses a unique gel-like texture and feel even in the absence of silicone elastomers. Moreover, the inclusion of a water-soluble surfactant together with an oil-absorbing powder surprisingly enhances the pickup, payoff and spreadability of the resulting product, while at the same time giving it a silky smooth feel. Finally, the composition possesses transfer resistance and long wear properties.

DETAILED DESCRIPTION OF THE INVENTION

Other than in the operating examples, or where otherwise indicated, all numbers expressing quantities of ingredients and/or reaction conditions are to be understood as being modified in all instances by the term "about".

"Cosmetic Pickup" as used herein means amount of cosmetic product received from its given container to its given applicator.

"Cosmetic payoff" as used herein means amount of cosmetic product dispensed from its given applicator (i.e. finger, brush) onto a keratinous substrate.

"Film former" or "film forming agent" or "film forming resin" as used herein means a polymer which, after dissolution in at least one solvent (such as, for example, water and organic solvents), leaves a film on the substrate to which it is applied, for example, once the at least one solvent evaporates, absorbs and/or dissipates on the substrate.

"Tackiness", as used herein, refers to the adhesion between two substances. For example, the more tackiness there is between two substances, the more adhesion there is between the substances.

"Keratinous substrates", as used herein, include but are not limited to, skin, hair and nails.

"Substituted" as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

As defined herein, stability is tested by placing the composition in a controlled environment chamber for 8 weeks at 25° C. In this test, the physical condition of the sample is inspected as it is placed in the chamber. The sample is then inspected again at 24 hours, 3 days, 1 week, 2 weeks, 4 weeks and 8 weeks. At each inspection, the sample is examined for abnormalities in the composition such as phase separation if the composition is in the form of an emulsion, bending or leaning if the composition is in stick form, melting, or syneresis (or sweating). The stability is further tested by repeating the 8-week test at 37° C., 40° C., 45° C., 50° C., and under freeze-thaw conditions. A composition is considered to lack stability if in any of these tests an abnormality that impedes functioning of the composition is observed. The skilled artisan will readily recognize an abnormality that impedes functioning of a composition based on the intended application.

"Volatile", as used herein, means having a flash point of less than about 100° C.

"Non-volatile", as used herein, means having a flash point of greater than about 100° C.

As used herein, the expression "at least one" means one or more and thus includes individual components as well as mixtures/combinations.

Other than in the operating examples, or where otherwise indicated, all numbers expressing quantities of ingredients and/or reaction conditions are to be understood as being modified in all instances by the term "about," meaning within 10% to 15% of the indicated number.

"Waterproof" as used herein refers to the ability to repel water and permanence with respect to water. Waterproof properties may be evaluated by any method known in the art for evaluating such properties. For example, a mascara composition may be applied to false eyelashes, which may then be placed in water for a certain amount of time, such as, for example, 20 minutes. Upon expiration of the pre-ascertained amount of time, the false eyelashes may be removed from the water and passed over a material, such as, for example, a sheet of paper. The extent of residue left on the material may then be evaluated and compared with other compositions, such as, for example, commercially available compositions. Similarly, for example, a composition may be applied to skin, and the skin may be submerged in water for a certain amount of time. The amount of composition remaining on the skin after the pre-ascertained amount of time may then be evaluated and compared. For example, a composition may be waterproof if a majority of the product is left on the wearer, e.g., eyelashes, skin, etc. In a preferred embodiment of the present invention, little or no composition is transferred from the wearer.

"Long wear" compositions as used herein, refers to compositions where color remains the same or substantially the same as at the time of application, as viewed by the naked eye, after an extended period of time. Long wear properties may be evaluated by any method known in the art for evaluating such properties. For example, long wear may be evaluated by a test involving the application of a composition to human hair, skin or lips and evaluating the color of the composition after an extended period of time. For example, the color of a composition may be evaluated immediately following application to hair, skin or lips and these characteristics may then be re-evaluated and compared after a certain amount of time. Further, these characteristics may be evaluated with respect to other compositions, such as commercially available compositions.

"Transfer resistance" as used herein refers to the quality exhibited by compositions that are not readily removed by contact with another material, such as, for example, a glass, an item of clothing or the skin, for example, when eating or drinking. Transfer resistance may be evaluated by any method known in the art for evaluating such. For example, transfer resistance of a composition may be evaluated by a "kiss" test. The "kiss" test may involve application of the composition to human keratin material such as hair, skin or lips followed by rubbing a material, for example, a sheet of paper, against the hair, skin or lips after expiration of a certain amount of time following application, such as 2 minutes after application. Similarly, transfer resistance of a composition may be evaluated by the amount of product transferred from a wearer to any other substrate, such as transfer from the hair, skin or lips of an individual to a collar when putting on clothing after the expiration of a certain amount of time following application of the composition to the hair, skin or lips. The amount of composition transferred to the substrate (e.g., collar, or paper) may then be evaluated and compared. For example, a composition may be transfer resistant if a majority of the product is left on the wearer's hair, skin or lips. Further, the amount transferred may be compared with that transferred by other compositions, such as commercially available compositions. In a preferred embodiment of the present invention, little or no composition is transferred to the substrate from the hair, skin or lips.

Polyamine Compound

According to the present invention, compositions comprising at least one polyamine compound are provided. In accordance with the present invention, the polyamine compound has at least two primary amine groups available to react with hydrophilic groups of the oil-soluble polar modified polymer.

According to particularly preferred embodiments, the polyamine compound is a polyalkyleneimine, preferably a C2-C5 polyalkyleneamine compound, more preferably a polyethyleneimine or polypropyleneimine. Most preferably, the polyalkylenamine is polyethyleneimine ("PEI"). The polyalkyleneamine compound preferably has an average molecular weight range of from 500-200,000, including all ranges and subranges therebetween.

According to preferred embodiments, compositions of the present invention contain polyethyleneimine compounds in the form of branched polymers. Commercially available examples of such polymers are available from BASF under the tradename LUPASOL or POLYIMIN. Non-limiting examples of such polyethyleneimines include Lupasol® PS, Lupasol® PL, Lupasol® PR8515, Lupasol® G20, Lupasol® G35.

According to other embodiments of the present invention, polyamines such as polyethyleneimines and polypropyleneimines can be in the form of dendrimers. Non-limiting examples of such dendrimers are manufactured by the company DSM, and/or are disclosed in U.S. Pat. No. 5,530,092 and U.S. Pat. No. 5,610,268, the contents of which are hereby incorporated by reference. Commercially available examples of such polymers include polyamidoamine or polypropyleneimine polymers from DENDRITECH sold under the STARBURST® name.

According to other embodiments of the present invention, derivatives of polyalkyleneamines are suitable polyamines. Such derivatives include, but are not limited to, alkylated derivatives, the addition products of alkylcarboxylic acids to polyalkyleneamines, the addition products of ketones and of aldehydes to polyalkyleneamines, the addition products of isocyanates and of isothiocyanates to polyalkyleneamines, the addition products of alkylene oxide or of polyalkylene oxide block polymers to polyalkyleneamines, quaternized derivatives of polyalkyleneamines, the addition products of a silicone to polyalkyleneamines, and copolymers of dicarboxylic acid and polyalkyleneamines. Even further suitable polyamines include, but are not limited to, polyvinylimidazoles (homopolymers or copolymers), polyvinylpyridines (homopolymers or copolymers), compounds comprising vinylimidazole monomers (see, for example, U.S. Pat. No. 5,677,384, hereby incorporated by reference), and polymers based on amino acids containing a basic side chain (preferably selected from proteins and peptides comprising at least 5%, preferably at least 10% of amino acids selected from histidine, lysine and arginine). Such suitable polyamines as described above include those disclosed and described in U.S. Pat. No. 6,162,448, the contents of which are hereby incorporated by reference. Commercially available examples of such polymers include polyvinylamine/formamide such as those sold under the Lupamine® name by BASF, chitosan from vegetable origin such as those sold under the Kiosmetine® or Kitozyme® names, or copolymer 845 sold by ISP.

According to preferred embodiments, the at least one polyamine compound is present in the composition of the present invention in an amount ranging from about 0.05 to about 10% by weight, more preferably from about 1 to about 8% by weight, more preferably from about 2 to about 5% by weight based on the total weight of the composition, including all ranges and subranges within these ranges.

Preferably, the amount of polyamine compound reacted with the oil-soluble polar modified polymer is such that at least two amine groups on the polyamine compound react with the oil-soluble polar modified polymer to form links or bonds between the amine groups and the hydrophilic groups of the oil-soluble polar modified polymer. The appropriate amount of polyamine compound to react with the oil-soluble polar modified polymer to obtain a reaction product can be easily determined, taking into account the number/amount of reactive amine groups on the polyamine compound and the number/amount of corresponding reactive groups on the oil-soluble polar modified polymer (for example, maleic anhydride groups). According to preferred embodiments, excess oil-soluble polar modified polymer (as determined by the relative number/amount of corresponding reactive groups on the polymer as compared to the reactive amine groups on the polyamine) is reacted with polyamine. Preferably, the polyamine to oil-soluble polar modified ratio is between 0.005 and 1, preferably between 0.006 and 0.5, and preferably between 0.007 and 0.1, including all ranges and subranges therebetween.

Oil-Soluble Polar Modified Polymer

According to the present invention, compositions comprising at least one oil-soluble polar modified polymer are provided. "Polar modified polymer" as used herein refers to a hydrophobic homopolymer or copolymer which has been modified with hydrophilic unit(s). "Oil-soluble" as used herein means that the polar modified polymer is soluble in oil.

Suitable monomers for the hydrophobic homopolymers and/or copolymers include, but are not limited to, cyclic, linear or branched, substituted or unsubstituted, C2-C20 compounds such as, for example, styrene, ethylene, propylene, isopropylene, butylene, isobutylene, pentene, isopentene, isoprene, hexene, isohexene, decene, isodecene, and octadecene, including all ranges and subranges therebetween. Preferably, the monomers are C2-C8 compounds, more preferably C2-C6 compounds, and most preferably C2-C4 compounds such as ethylene, propylene and butylene.

Suitable hydrophilic unit(s) include, but are not limited to, maleic anhydride, acrylates, alkyl acrylates such as, for example, methyl acrylate, ethyl acrylate, propyl acrylate, and butyl acrylate, and polyvinylpyrrolidone (PVP).

According to the present invention, the polar modified polymer is oil-soluble: that is, the polymer does not contain a sufficient amount of hydrophilic unit(s) to render the entire polymer water-soluble or oil-insoluble. According to preferred embodiments, the polar modified polymer contains the same amount of hydrophobic monomer as hydrophilic unit (1:1 ratio) or more hydrophobic monomer than hydrophilic unit. According to particularly preferred embodiments, the polar modified polymer contains 50% or less hydrophilic unit(s) (based on weight of the polymer), 40% or less hydrophilic unit(s), 30% or less hydrophilic unit(s), 20% or less hydrophilic unit(s), 10% or less hydrophilic unit(s), 5% or less hydrophilic unit(s), 4% or less hydrophilic unit(s), or 3% or less hydrophilic unit(s).

Preferably, the polar modified polymer has from about 0.5% to about 10% hydrophilic units, more preferably from about 1% to about 8% hydrophilic units by weight with respect to the weight of the polymer, including all ranges and subranges therebetween. Particularly preferred hydrophilically modified polymers are ethylene and/or propylene homopolymers and copolymers which have been modified with maleic anhydride units.

According to preferred embodiments of the present invention, the polar modified polymer is a wax. According to particularly preferred embodiments, the polar modified wax is made via metallocene catalysis, and includes polar groups or units as well as a hydrophobic backbone. Suitable modified waxes include those disclosed in U.S. patent application publication no. 20070031361, the entire contents of which is hereby incorporated by reference. Particularly preferred polar modified waxes are C2-C3 polar modified waxes.

In accordance with preferred embodiments of the present invention, the polar modified wax is based upon a homopolymer and/or copolymer wax of hydrophobic monomers and has a weight-average molecular weight Mw of less than or equal to 25000 g/mol, preferably of 1000 to 22 000 g/mol and particularly preferably of 4000 to 20,000 g/mol, a number-average molecular weight Mn of less than or equal to 15 000 g/mol, preferably of 500 to 12 000 g/mol and particularly preferably of 1000 to 5000 g/mol, a molar mass distribution Mw/Mn in the range from 1.5 to 10, preferably from 1.5 to 5, particularly preferably from 1.5 to 3 and especially preferably from 2 to 2.5, which have been obtained by metallocene catalysis. Also, the polar modified wax preferably has a melting point above 75° C., more preferably above 90° C. such as, for example, a melting point between 90° C. and 160° C., preferably between 100° C. and 150° C., including all ranges and subranges therebetween.

In the case of a copolymer wax, it is preferable to have, based on the total weight of the copolymer backbone, 0.1 to 30% by weight of structural units originating from the one monomer and 70.0 to 99.9% by weight of structural units originating from the other monomer. Such homopolymer and copolymer waxes can be made, for example, by the process described in EP 571 882, the entire contents of which is hereby incorporated by reference, using the metallocene catalysts specified therein. Suitable preparation processes include, for example, suspension polymerization, solution polymerization and gas-phase polymerization of olefins in the presence of metallocene catalysts, with polymerization in the monomers also being possible.

Polar modified waxes can be produced in a known manner from the hompopolymers and copolymers described above by oxidation with oxygen-containing gases, for example air, or by graft reaction with polar monomers, for example maleic acid or acrylic acid or derivatives of these acids. The polar modification of metallocene polyolefin waxes by oxidation with air is described, for example, in EP 0 890 583 A1, and the modification by grafting is described, for example, in U.S. Pat. No. 5,998,547, the entire contents of both of which are hereby incorporated by reference in their entirety.

Acceptable polar modified waxes include, but are not limited to, homopolymers and/or copolymers of ethylene and/or propylene groups which have been modified with hydrophilic units such as, for example, maleic anhydride, acrylate, methacrylate, polyvinylpyrrolidone (PVP), etc. Preferably, the C2-C3 wax has from about 0.5% to about 10% hydrophilic units, more preferably from about 1% to about 8% hydrophilic units by weight with respect to the weight of the wax, including all ranges and subranges therebetween. Particularly preferred hydrophilically modified waxes are ethylene and/or propylene homopolymers and copolymers which have been modified with maleic anhydride units.

Particularly preferred C2-C3 polar modified waxes for use in the present invention are polypropylene and/or polyethylene-maleic anhydride modified waxes ("PEMA," "PPMA," "PEPPMA") commercially available from Clariant under the trade name LICOCARE or LICOCENE, Specific examples of such waxes include products marketed by Clariant under the LicoCare name having designations such as PP207.

Other suitable polar modified polymers include, but are not limited to A-C 573 A (ETHYLENE-MALEIC ANHYDRIDE COPOLYMER; Drop Point, Mettler: 106° C.) from Honeywell, A-C 596 A (PROPYLENE-MALEIC ANHYDRIDE COPOLYMER; Drop Point, Mettler: 143° C.) from Honeywell, A-C 597 (PROPYLENE-MALEIC ANHYDRIDE COPOLYMER; Drop Point, Mettler: 141° C.) from Honeywell, ZeMac® copolymers (from VERTELLUS) which are 1:1 copolymers of ethylene and maleic anhydride, polyisobutylene-maleic anhydride sold under the trade name ISOBAM (from Kuraray), polyisoprene-graft-maleic anhydride sold by Sigma Aldrich, poly(maleic anhydride-octadecene) sold by Chevron Philips Chemcial Co., poly (ethylene-co-butyl acrylate-co-maleic anhydride) sold under the trade name of Lotader (e.g. 2210, 3210, 4210, and 3410 grades) by Arkema, copolymers in which the butyl acrylate is replaced by other alkyl acrylates (including methyl acrylate [grades 3430, 4404, and 4503] and ethyl acrylate [grades 6200, 8200, 3300, TX 8030, 7500, 5500, 4700, and 4720) also sold by Arkema under the Lotader name, and isobutylene maleic anhydride copolymer sold under the name ACO-5013 by ISP.

According to other embodiments of the present invention, the polar modified polymer is not a wax. In accordance with these embodiments of the present invention, the polar modified polymer is based upon a homopolymer and/or copolymer of hydrophobic monomer(s) and has a weight-average molecular weight Mw of less than or equal to 1,000,000 g/mol, preferably of 1000 to 250,000 g/mol and particularly preferably of 5,000 to 50,000 g/mol, including all ranges and subranges therebetween.

In accordance with these embodiments, the polar modified polymer can be of any form typically associated with polymers such as, for example, block copolymer, a grafted copolymer or an alternating copolymer. For example, the polar modified polymer can contain a hydrophobic backbone (such as polypropylene and/or polyethylene) onto which hydrophilic groups (such as maleic anhydride) have been attached by any means including, for example, grafting. The attached groups can have any orienation (for example, atactic, isotactic or syndiotactic along the backbone).

Preferably, the polar modified polymer(s) represent from about 3% to about 20% of the total weight of the composition, more preferably from about 5% to about 18% of the total weight of the composition, and most preferably from about 4% to about 15%, including all ranges and subranges therebetween.

Water

The composition of the present invention also contains water. Preferably, water is present in an amount sufficient to solubilize the polyamine present in the composition. Also preferably, sufficient water is present to form a water-in-oil emulsion. The water is typically employed in an amount of from about 0.5% to about 50% by weight, such as from about 1% to about 40% by weight, such as from about 2% to about 30% by weight, including all ranges and subranges therebetween, all weights being based on the total weight of the composition.

Volatile Solvents Other Than Water

The compositions of the present invention comprise at least one volatile solvent. The at least one volatile solvent is preferably chosen from a volatile silicone oil or a volatile non-silicone oil.

Suitable volatile silicone oils include, but are not limited to, linear or cyclic silicone oils having a viscosity at room temperature less than or equal to 6 cSt and having from 2 to 7 silicon atoms, these silicones being optionally substituted with alkyl or alkoxy groups of 1 to 10 carbon atoms. Specific oils that may be used in the invention include octamethyltetrasiloxane, decamethylcyclopentasiloxane, dodecamethylcyclohexasiloxane, heptamethyloctyltrisiloxane, hexamethyldisiloxane, decamethyltetrasiloxane, dodecamethylpentasiloxane and their mixtures. Other volatile oils which may be used include KF 96A of 6 cSt viscosity, a commercial product from Shin Etsu having a flash point of 94° C. Preferably, the volatile silicone oils have a flash point of at least 40° C.

Non-limiting examples of volatile silicone oils are listed in Table 1 below.

TABLE 1

| Compound | Flash Point (° C.) | Viscosity (cSt) |
| --- | --- | --- |
| Octyltrimethicone | 93 | 1.2 |
| Hexyltrimethicone | 79 | 1.2 |
| Decamethylcyclopentasiloxane (cyclopentasiloxane or D5) | 72 | 4.2 |
| Octamethylcyclotetrasiloxane (cyclotetradimethylsiloxane or D4) | 55 | 2.5 |
| Dodecamethylcyclohexasiloxane (D6) | 93 | 7 |
| Decamethyltetrasiloxane (L4) | 63 | 1.7 |
| KF-96 A from Shin Etsu | 94 | 6 |
| PDMS (polydimethylsiloxane) DC 200 (1.5 cSt) from Dow Corning | 56 | 1.5 |
| PDMS DC 200 (2 cSt) from Dow Corning | 87 | 2 |
| PDMS DC 200 (3 St) from Dow Corning | 102 | 3 |

Suitable volatile non-silicone oils may be selected from volatile hydrocarbon oils, alcohols, volatile esters and volatile ethers. Examples of such volatile non-silicone oils include, but are not limited to, volatile hydrocarbon oils having from 8 to 16 carbon atoms and their mixtures and in particular branched $C_8$ to $C_{16}$ alkanes such as $C_8$ to $C_{16}$ isoalkanes (also known as isoparaffins), isododecane, isodecane, isohexadecane, and for example, the oils sold under the trade names of Isopar or Permethyl, the $C_8$ to $C_{16}$ branched esters such as isohexyl or isodecyl neopentanoate and their mixtures. Preferably, the volatile non-silicone oils have a flash point of at least 40° C.

Non-limiting examples of volatile non-silicone oils are listed in Table 2 below.

TABLE 2

| Compound | Flash Point (° C.) |
|---|---|
| Isododecane | 43 |
| Propylene glycol n-butyl ether | 60 |
| Ethyl 3-ethoxypropionate | 58 |
| Propylene glycol methylether acetate | 46 |
| Isopar L (isoparaffin C11-C13) | 62 |
| Isopar H (isoparaffin C11-C12) | 56 |

In general, the at least one volatile solvent is preferably present in the composition in an amount of from about 20 to about 90% by weight, such as from about 30 to about 80% by weight, and from about 35 to about 75% by weight, including all ranges and subranges therebetween, all weights being based on the total weight of the composition.

According to preferred embodiments of the present invention, the composition of the present invention comprises a blend of at least two volatile solvents having different flash points. The blend of volatile solvents will typically be present in an amount of from about 20 to about 90% by weight, such as from about 30 to about 80% by weight, and from about 35 to about 75% by weight, based on the total weight of the composition, as discussed above.

Reaction Product

According to preferred embodiments of the present invention, the oil-soluble polar modified polymer is reacted with the polyamine compound, in the presence of water in, at minimum, an amount sufficient to solubilize the polyamine, to form a reaction product. In accordance with the preferred embodiments, the reaction product is water-insoluble.

Although not wanting to be bound by any particular theory, it is believed that at a temperature below 100° C., the reaction of the oil-soluble polar modified polymer with the primary amine group of the polyamine opens the anhydride ring to form a half acid and half amide crosslinked product. However, at a temperature above 100° C., the reaction of the oil-soluble polar modified polymer with the primary amine group of the polyamine opens the anhydride ring to form an imide crosslinked product. The former product is preferred over the latter product. It is not necessary for all amine groups and all hydrophilic groups to react with each other to form the reaction product. Rather, it is possible that the composition may contain free polyamine and/or free oil-soluble polar modified polymer in addition to the reaction product.

Although not wanting to be bound by any particular theory, it is also believed that the polyamine(s) can be non-covalently assembled with the polar modified polymer(s) by electrostatic interaction between an amine group of the polyamine and a hydrophilic group (for example, carboxylic acid group associated with maleic anhydride groups) of the polar modified polymer to form a supramolecule. For example, with specific reference to maleic anhydride groups, in the presence of water these groups can open to form dicarboxylic acid groups which can interact with protonated primary amines of the polyamine through ionic interaction to form a polymer-polymer complex with hydrophilic core crosslinkers and a hydrophobic network that act as supramolecular capsule. If a large amount of maleic anhydride groups are present, the secondary amine groups of polyamine are also protonated and interact with alkyl carboxylates.

According to preferred embodiments, the oil-soluble polar modified polymer is in an oil carrier, and the polyamine compound is in an aqueous carrier, and the reaction occurs by combining the oil carrier and the aqueous carrier. Because the oil-soluble polar modified polymer is typically solid at room temperature, the oil carrier is preferably heated to liquefy the polymer prior to combination with the aqueous carrier. Preferably, the oil carrier is heated beyond the melting point of the oil-soluble polar modified polymer, typically up to about 80° C., 90° C. or 100° C.

Without intending to be bound by any particular theory, it is believed that the reason for this is that due to the chemical and physical reactions which take place when the oil-soluble polar modified polymer is combined with the polyamine, the subsequent reaction product that is formed is surprisingly and unexpectedly able to entrap large amounts of water molecules within its hydrophobic matrix. The resultant product is eminently capable of forming a film, is self-emulsifying, waterproof. Moreover, the product is both stable and capable of carrying various types of ingredients.

Non-Volatile Solvent

The cosmetic compositions of the present invention comprise at least one non-volatile solvent. The non-volatile solvent is capable of solubilzing the oil-soluble polar modified polymer. As used herein, the term "non-volatile" means having a flash point of greater than about 100° C. The at least one non-volatile solvent typically comprises at least one non-volatile oil.

Examples of non-volatile oils that may be used in the present invention include, but are not limited to, polar oils such as:

hydrocarbon-based plant oils with a high triglyceride content consisting of fatty acid esters of glycerol, the fatty acids of which may have varied chain lengths, these chains possibly being linear or branched, and saturated or unsaturated; these oils are especially wheat germ oil, corn oil, sunflower oil, karite butter, castor oil, sweet almond oil, macadamia oil, apricot oil, soybean oil, rapeseed oil, cottonseed oil, alfalfa oil, poppy oil, pumpkin oil, sesame seed oil, marrow oil, avocado oil, hazelnut oil, grape seed oil, blackcurrant seed oil, evening primrose oil, millet oil, barley oil, quinoa oil, olive oil, rye oil, safflower oil, candlenut oil, passion flower oil or musk rose oil; or caprylic/capric acid triglycerides, for instance those sold by the company Stearineries Dubois or those sold under the names Miglyol 810, 812 and 818 by the company Dynamit Nobel;

synthetic oils or esters of formula $R_5COOR_6$ in which $R_5$ represents a linear or branched higher fatty acid residue containing from 1 to 40 carbon atoms, including from 7 to 19 carbon atoms, and $R_6$ represents a branched hydrocarbon-based chain containing from 1 to 40 carbon atoms, including from 3 to 20 carbon atoms, with $R_6+R_7 \square 10$, such as, for example, Purcellin oil (cetostearyl octanoate), isononyl isononanoate, $C_{12}$ to $C_{15}$ alkyl benzoate, isopropyl myristate, 2-ethylhexyl palmitate, and octanoates, decanoates or ricinoleates of alcohols or of polyalcohols; hydroxylated esters, for instance isostearyl lactate or diisostearyl malate; and pentaerythritol esters;

synthetic ethers containing from 10 to 40 carbon atoms; $C_8$ to $C_{26}$ fatty alcohols, for instance oleyl alcohol; and mixtures thereof.

Further, examples of non-volatile oils that may be used in the present invention include, but are not limited to, non-polar oils such as branched and unbranched hydrocarbons and hydrocarbon waxes including polyolefins, in particular Vaseline (petrolatum), paraffin oil, squalane, squalene, hydrogenated polyisobutene, hydrogenated polydecene, polybutene, mineral oil, pentahydrosqualene, and mixtures thereof.

The at least one non-volatile solvent is preferably present in the composition of the invention in an amount of from about 1% to about 20% by weight, such as from about 1.5% to about 10% by weight, such as from about 2% to about 5% by weight, including all ranges and subranges therebetween, all weights being based on the total weight of the composition.

Water Soluble Surfactant

The compositions of the present invention also comprise a water-soluble surfactant. Any type of surfactant that is hydrophilic enough to disperse in water may be employed as a water-soluble surfactant. These include nonionic, cationic, anionic, zwitterionic, and amphoteric surfactants.

Particularly preferred are phosphate surfactants.

Preferably, the at least one phosphate surfactant is selected from monoalkyl phosphates, dialkyl phosphates, salts of monoalkyl phosphates, salts of dialkyl phosphates, and mixtures thereof. More preferably, the monoalkyl phosphates and dialkyl phosphates comprise one or more linear or branched and aliphatic and/or aromatic alkyl chains having from 8 to 22 carbon atoms. According to preferred embodiments, the phosphate surfactant(s) can be neutralized with organic or inorganic bases such as, for example, potassium hydroxide, sodium hydroxide, triethanolamine, arginine, lysine and N-methylglucamine to form the aforementioned salts.

Suitable examples of phosphate surfactants include, but are not limited to, monolauryl phosphate, such as the product sold under the name MAP 20® by Kao Chemicals, the potassium salt of dodecyl phosphate, such as the mixture of mono- and diester (predominantly diester) sold under the name Crafol AP-31® by Cognis, the octyl monoester and the octyl diester of phosphoric acid, such as the mixture sold under the name Crafol AP-20® by Cognis, the ethoxylated (7 mol. of EO) 2-butyloctanol monoester and the ethoxylated (7 mol. of EO) 2-butyloctanol diester of phosphoric acid, such as the mixture sold under the name Isofol 12 7 EO-Phosphate Ester® by Condea, the potassium or triethanolamine salts of monoalkyl ($C_{12}$-$C_{13}$) phosphate, such as the product sold under the references Arlatone MAP 230K-40® and Arlatone MAP 230T-60® by Uniqema, potassium lauryl phosphate, such as the product as a 40% aqueous solution sold under the name Dermalcare MAP XC99/09® by Rhodia Chimie, potassium cetyl phosphate, such as the product sold under the name Arlatone MAP 160K® by Uniqema, and the mixtures of these surfactants.

The water soluble surfactant is preferably present in an amount of from about 0.5% to about 10% by weight, such as from about 1% to about 5% by weight, such as from about 2% to about 4% by weight, including all ranges and subrangs therebetween, all weights being based on the total weight of the composition.

It has been surprisingly discovered that the addition of a water soluble surfactant in the present invention improves the payoff, pickup and texture of the composition, without reducing the wear property of the composition.

Oil Absorbing Powders

The compositions of the present invention also include at least one oil absorbing powder. Oil absorbing powders that may be used in the compositions of the invention include, for example, silica powder; talc; polyamide particles and especially those sold under the name Orgasol by the company Atochem; polyethylene powders; microspheres based on acrylic copolymers, such as those based on ethylene glycol dimethacrylate/lauryl methacrylate copolymer sold by the company Dow Corning under the name Polytrap; expanded powders such as hollow microspheres and especially the microspheres sold under the name Expancel by the company Kemanord Plast or under the name Micropearl F 80 ED by the company Matsumoto; powders of natural organic materials such as crosslinked or noncrosslinked corn starch, wheat starch or rice starch, such as the powders of starch crosslinked with octenyl succinate anhydride, sold under the name Dry-Flo by the company National Starch; silicone resin microbeads such as those sold under the name Tospearl by the company Toshiba Silicone; clays (bentone, laponite, saponite, etc.); and mixtures thereof.

The oil absorbing powder is preferably present in an amount of from about 0.5% to about 20% by weight, such as from about 1% to about 10% by weight, such as from about 3% to about 5% by weight, including all ranges and subrangs therebetween, all weights being based on the total weight of the composition.

Optional Ingredients

The composition of the present invention may also include any one, or more, optional ingredients. Examples thereof include, but are not limited to, colorants such as dyes and pigments, co-solvents (volatile and/or non-volatile), waxes, plasticizers, preservatives, fillers, active ingredients such as those used to treat skin and hair and sunscreens.

It has surprisingly been discovered that the composition of the present invention is highly transfer resistant and long wearing, with good cosmetic pickup and payoff, and possesses a unique texture and feel even in the absence of silicone resins, silicone elastomers and/or gelling agents. Moreover, it has also been unexpectedly discovered that the addition of a water soluble surfactant together with an oil absorbing powder in the present invention improves the payoff, pickup and spreadability of the composition, without reducing the wear property of the composition, while at the same time giving it a silky smooth feel.

The composition of the present invention may be used for any application in which it is desirable to employ a waterproof film, capable of carrying insoluble ingredients such as, for example, pigments, and which is stable, easily spreadable, and comfortable to apply. Preferably, the composition of the present invention is employed as a foundation.

The present invention is further described in terms of the following non-limiting examples. Unless otherwise indicated, all parts and percentages are on a weight-by-weight percentage basis.

EXAMPLE 1

Transfer Resistance Foundation Properties: Creamy, Soft, Bouncy Gel

| | |
|---|---|
| Isododecane | 49.25 |
| isohexadecane | 1.95 |
| PP207* PROPYLENE MALEIC ANHYDRIDE COPOLYMER | 6.5 |
| Sunsphere Silica | 3 |
| DI Water | 20.5 |
| Lupasol G 35 PEI (PolyEthyleneImine) (50% SOLID/50% WATER) | 4 |
| Potassium Cetyl Phosphate | 3 |
| Simethicone | 0.3 |
| TITANIUM DIOXIDE | 7.82 |
| IRON OXIDES | 1.46 |
| IRON OXIDES | 0.52 |
| IRON OXIDES | 0.2 |
| DISODIUM EDTA | 0.20 |
| Glycerin | 0.50 |
| PHENOXY-2 ETHANOL | 0.40 |
| CHLORPHENESIN | 0.20 |
| ETHYL PARABEN | 0.2 |
| | 100 |

*PP207 is a linear polypropylene-ethylene-maleic anhydride copolymer wax commercially available from Clariant under the tradename LICOCARE PP207 LP 3349.

Procedure

In container A, PP207 was melted in the isohexadecane and isododecane until fully dissolved. The temperature was brought to 90° C.

While maintaining the temperature, the pigment grind were added to container A along with the oil absorbing powder until fully dissolved.

In separate container B, LUPASOL G 35 PEI (PolyEthyleneImine), water soluble surfactant (AMPHISOL K), simethicone, preservatives, glycerin and water were mixed at room temperature;

B was added to A dropwise with a pipet at high sheer (~700 rpm);

Heat was maintained at 70-80° C. for 20 minutes while maintaining high sheer mixing;

The mixture was cooled to room temperature while mixing.

Transfer Resistant Data

The compositions listed above were tested for transfer resistance following the expert panel methodology for testing. The panelists were all then given a piece of cloth. Panelist then spread 0.1 ml of foundation onto their face and waited 10 minutes. After 10 minutes, panelists were then asked to run the cloth over their face, and then grade their cloth for then amount of foundation transferred thereon.

Results

Following the expert panel method, the formulations above were shown to have higher transfer resistant properties than commercially available top long wearing, transfer resistant foundation products on the market.

EXAMPLE 2

| UNDECANE (and) TRIDECANE | 29.25 |
|---|---|
| isododecane | 20 |
| isohexadecane | 1.95 |
| PP207* PROPYLENE MALEIC ANHYDRIDE COPOLYMER | 6.5 |
| Sunsphere Silica | 3 |
| DI Water | 20.5 |
| Lupasol G 35 PEI (PolyEthyleneImine) (50% SOLID/50% WATER | 4 |
| Potassium cetyl phosphate | 3 |
| Simethicone | 0.3 |
| TITANIUM DIOXIDE | 7.82 |
| IRON OXIDES | 1.46 |
| IRON OXIDES | 0.52 |
| IRON OXIDES | 0.2 |
| DISODIUM EDTA | 0.20 |
| propylene glycol | 0.50 |
| PHENOXY-2 ETHANOL | 0.40 |
| CHLORPHENESIN | 0.20 |
| ETHYL PARABEN | 0.2 |
| | 100 |

EXAMPLE 3

| isododecane | 30 |
|---|---|
| MethylTrimethicone | 13 |
| PP207* | 8.6 |
| SILICA | 4 |
| METHYL METHACRYLATE CROSSPOLYMER | 2.5 |
| SILICA | 1.5 |
| Potassium Cetyl Phosphate | 2.5 |
| TITANIUM DIOXIDE | 7.82 |
| IRON OXIDES | 1.46 |
| IRON OXIDES | 0.52 |
| IRON OXIDES | 0.2 |

-continued

| DI Water | 17.5 |
|---|---|
| Polyethyleneimine (LUPASOL G 35) | 1.1 |
| DISODIUM EDTA | 0.20 |
| glycerin | 3.50 |
| propylene glycol | 1.00 |
| PHENOXY-2 ETHANOL | 0.50 |
| methylparaben | 0.20 |
| CHLORPHENESIN | 0.20 |
| ETHYL PARABEN | 0.2 |
| salt | 0.50 |

Shine Control Data:
Comparing the Product Over Time
On the deviations (Tn-T0)±standard deviation

| Product | Matt appearance (Timm-T0) | Matt appearance (T3h-T0) |
|---|---|---|
| Example 3 | −11.31 ± 3.69 | −8.17 ± 4.87 |

Matt appearance: changes and hold over time

On the deviations (Tn-T0)±standard deviation

| Product | Hold (T3h-Timm) | Significance of hold/0 |
|---|---|---|
| Example 3 | 3.14 ± 3.10 | S (α = 0.05) |

PROCEDURE

In container A, PP207 was melted in the isohexadecane, undecane (and) tridecane, and isododecane until fully dissolved. The temperature was brought to 90° C.

While maintaining the temperature, the pigment grind were added to container A along with the oil absorbing powder until fully dissolved.

In separate container B, LUPASOL G 35 PEI (PolyEthyleneImine), water soluble surfactant (AMPHISOL K), simethicone, preservatives, glycerin and water were mixed at room temperature;

B was added to A dropwise with a pipet at high sheer (~700 rpm);

Heat was maintained at 70-80° C. for 20 minutes while maintaining high sheer mixing;

The mixture was cooled to room temperature while mixing.

Transfer Resistant Data

The compositions listed above were tested for transfer resistance following the expert panel methodology for testing. The panelists were all then given a piece of cloth. Panelist then spread 0.1 ml of foundation onto their face and waited 10 minutes. After 10 minutes, panelists were then asked to run the cloth over their face, and then grade their cloth for then amount of foundation transferred thereon.

Results

Following the expert panel method, the formulations above were shown to have higher transfer resistant properties than commercially available top long wearing, transfer resistant foundation products on the market.

What is claimed is:

1. A cosmetic composition comprising:
 (a) a reaction product of at least one polyamine having a molecular weight of from 500-200,000 and at least one oil-soluble polar modified polymer, wherein the reaction product is water-insoluble half acid and half amide crosslinked reaction product and wherein the polar modified polymer comprises maleic anhydride groups and the reaction product is produced by reacting the maleic anhydride groups of the polar modified polymer with primary amine group of the polyamine in the presence of water and at a temperature below 100° C. such that dicarboxylic acid groups associated with the maleic anhydride groups open to interact with protonated primary amines of the polyamine through ionic interaction to form a hydrophobic network that act as supramolecular capsule;
(b) water in an amount of from 0.5 to 50% by weight, based on the weight of the composition;
(c) at least one volatile solvent other than water;
(d) at least one non-volatile solvent capable of solubilizing the oil-soluble polar modified polymer;
(e) at least one water soluble surfactant;
(f) at least one colorant; and
(g) at least one oil absorbing powder.

2. The composition of claim 1, wherein the polyamine is a branched polyethyleneimine.

3. The composition of claim 1, wherein the composition is made using from 0.05 to about 10% by weight, based on the weight of the composition, of the polyamine.

4. The composition of claim 1, wherein the composition is made using from 3 to about 20% by weight, based on the weight of the composition, of the oil-soluble polar modified polymer.

5. The composition of claim 1, wherein the non-volatile solvent is a non-volatile oil.

6. The composition of claim 1, wherein the non-volatile solvent is present in an amount of from 1.5 to 10% by weight, based on the weight of the composition.

* * * * *